(12) United States Patent
O'Lenick et al.

(10) Patent No.: US 8,025,870 B2
(45) Date of Patent: Sep. 27, 2011

(54) VINYL ETHER SILICONE POLYMERS

(75) Inventors: Kevin Anthony O'Lenick, Dacula, GA (US); Anthony J. O'Lenick, Jr., Dacula, GA (US)

(73) Assignee: Siltech Corporation, Toronto, Ontario (CA)

( * ) Notice: Subject to any disclaimer, the term of this patent is extended or adjusted under 35 U.S.C. 154(b) by 294 days.

(21) Appl. No.: 12/459,481

(22) Filed: Jul. 2, 2009

(65) Prior Publication Data
US 2011/0002867 A1 Jan. 6, 2011

(51) Int. Cl.
*C08G 77/06* (2006.01)

(52) U.S. Cl. .......... 424/70.12; 556/445; 528/15; 528/31

(58) Field of Classification Search .................. 528/15, 528/31; 556/445; 424/70.12
See application file for complete search history.

(56) References Cited

U.S. PATENT DOCUMENTS

| 2,017,355 | A |   | 12/1934 | Reppe |   |
|---|---|---|---|---|---|
| 2,970,150 | A | * | 1/1961 | Bailey | 549/215 |
| 3,929,851 | A | * | 12/1975 | Atherton et al. | 556/454 |
| 4,004,059 | A | * | 1/1977 | Deiner et al. | 442/80 |
| 2006/0160976 | A1 | * | 7/2006 | Berg-Schultz et al. | 528/10 |

\* cited by examiner

*Primary Examiner* — Margaret Moore

(57) ABSTRACT

The present invention is directed to a series of vinyl ether based silicone polymers and their use in personal care applications. They are prepared by the hydrosilylation reaction of a vinyl ether and a silanic hydrogen compound. The compounds find use in personal care applications.

6 Claims, No Drawings

VINYL ETHER SILICONE POLYMERS

GOVERNMENT SPONSORSHIP

None

FIELD OF THE INVENTION

The present invention is directed to a series of vinyl ether based silicone polymers and their use in personal care applications.

BACKGROUND OF THE INVENTION

Dimethicone compounds conform to the following structure:

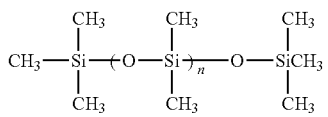

Silicone fluids, also called silicone oils, or simple silicone are sold by their viscosity and range from 0.65 cst to 1,000,000 cst. If blending two different viscosity fluids does not make the product the viscosity is related to molecular weight. The viscosity allows for an approximate calculation of the value of "n". The data is shown below.

| Viscosity 25 C. (Centistokes) | Approximate Molecular Weight | Approximate "n" Value | Compound |
|---|---|---|---|
| 5 | 800 | 9 | $MD_9M$ |
| 50 | 3,780 | 53 | $MD_{53}M$ |
| 100 | 6,000 | 85 | $MD_{85}M$ |
| 200 | 9,430 | 127 | $MD_{127}M$ |
| 350 | 13,650 | 185 | $MD_{185}M$ |
| 500 | 17,350 | 230 | $MD_{230}M$ |
| 1,000 | 28,000 | 375 | $MD_{375}M$ |
| 10,000 | 67,700 | 910 | $MD_{910}M$ |
| 60,000 | 116,500 | 1,570 | $MD_{1570}M$ |
| 100,000 | 139,050 | 1,875 | $MD_{1875}M$ |

One difficulty that is encountered is that these materials are insoluble in oils, water and in fluoro compounds.

This complication has resulted in difficulty in getting the properties of silicone, including spreadability and feel into systems that contain water or oil.

Molecules that contain water soluble, oil soluble and silicone soluble groups contain in one molecule three mutually insoluble groups. The concept of "hydrophilic and "hydrophobic" is related to water soluble, and in systems containing silicone needs to be expanded to include silicone compounds.

| Hydrophilic (water loving) | Hydrophobic (water hating) |
|---|---|
| Oleophilic (oil loving) | Oleophobic (oil hating) |
| Siliphilic (silicone loving) | Siliphobic (silicone hating) |

The way to improve solubility of silicone compounds in other types of solvents is to make molecules that contain silicone groups and groups soluble in the other solvent. Such molecules are amphilic, and have desirable properties.

To make a molecule soluble in oils, an oil soluble alkyl group is reacted onto the silicone backbone. A typical structure is shown:

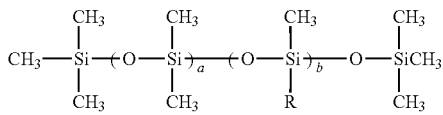

wherein:
R is $-(CH_2)_m-CH_3$;
m is an integer ranging from 7 to 44.

Some of the undesirable attributes of these products include:

1. They are based upon alpha olefin, $CH_2=CH-(CH_2)_{m-2}-CH_3$, an impure substance and can contain up to 20% unreactive alkane $CH_3-(CH_2)_{m-1}-CH_3$.

2. The alkyl group contains no polar groups making them of limited application is solubilizing organic materials that have polarity.

The present invention overcomes these problems and offers unique cosmetic aesthetics by replacing the alkyl group with an alkyl ether group. The raw material used to make the compounds of the present invention are vinyl ethers. They are pure materials (contain no alkane) and have a polar oxygen atom present in the backbone. They satisfy a long felt need n the industry for a chemically pure, polar oil soluble product.

The vinyl ethers useful as raw materials for the synthesis of the compounds of the present invention conform to the following structure:

$$CH_2=CH-O-(CH_2)_zCH_3$$

These compounds are made by the reaction of the alcohol (which is natural, derived from triglycerides) with acetylene. The chemistry is referred to as Reppe chemistry and is the topic of U.S. Pat. No. 2,017,335 issued to Reppe Dec. 8, 1934, incorporated herein by reference.

The reaction is applicable to both aliphatic and aromatic alcohols, primary and secondary alcohols, and phenols. Potassium hydroxide is employed as the catalyst. Ethers and esters and secondary amines also react with acetylene under pressure. For example, the reaction between methyl alcohol and acetylene goes very smoothly at about 200° C. to give methyl vinyl ether in the presence of KOH:

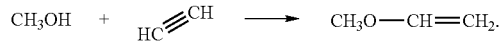

Additional patents related to this chemistry to Reppe include

U.S. Pat. No. 1,941,108 entitled Production of Vinyl Ethers;
U.S. Pat. No. 1,959,927 entitled Production of Vinyl Ethers;
U.S. Pat. No. 2,021,869 entitled Production of Vinyl Ether;
U.S. Pat. No. 2,066,076 entitled Producing Vinyl Ethers, all incorporated herein by reference.

These materials have been heretofore not attached to silicone to make the polymers of the present invention addressing the long felt need in the personal care market and providing the desirable unexpected benefits described above.

THE INVENTION

OBJECTIVE OF THE INVENTION

The object of the present invention is to provide a series of alkyl ether based silicone polymers.

Another object of the present invention is to provide a process for treating hair and skin with a series of alkyl ether based silicone polymers.

Other objects of the present invention will become apparent as one reads the disclosure.

SUMMARY OF THE INVENTION

The present invention is directed to a series of alkyl ether based silicone polymers. These materials are made by the hydrosilylation of vinyl ethers, reacted with silanic hydrogen containing polymers.

DETAILED DESCRIPTION OF THE INVENTION

The present invention is directed to a ether alkyl silicone conforming to the following structure;

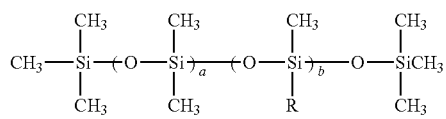

wherein:
R is —$(CH_2)_2$—O—$(CH_2)_z$—$CH_3$;
z is an integer ranging from 0 to 44;
a is an integer ranging from 0 to 2,000;
b is an integer ranging from 1 to 50.

The present invention is also directed to a ether alkyl silicone conforming to the following structure;

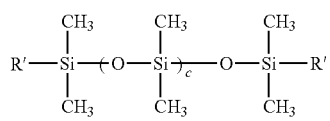

wherein:
R' is —$(CH_2)_2$—O—$(CH_2)_z$—$CH_3$;
z is an integer ranging from 0 to 44;
c is an integer ranging from 0 to 2,000.

The present invention is also directed to a process for conditioning hair and skin, which comprises contacting the hair or skin with an effective conditioning concentration of to a ether alkyl silicone conforming to the following structure;

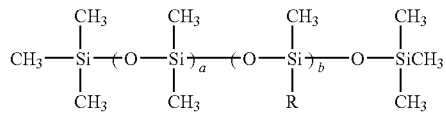

wherein:
R is —$(CH_2)_2$—O—$(CH_2)_z$—$CH_3$;
z is an integer ranging from 0 to 44;
a is an integer ranging from 0 to 2,000;
b is an integer ranging from 1 to 50;
said effective conditioning concentration ranging from 0.1 to 20% by weight The present invention is also directed to a process for conditioning hair and skin, which comprises contacting the hair or skin with an effective conditioning concentration of an ether alkyl silicone conforming to the following structure;

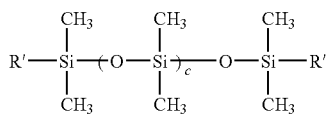

wherein:
R' is —$(CH_2)_2$—O—$(CH_2)_z$—$CH_3$;
z is an integer ranging from 0 to 44;
c is an integer ranging from 0 to 2,000;
said effective conditioning concentration ranging from 0.1 to 20% by weight.

PREFERRED EMBODIMENTS

In a preferred embodiment a ranges from 1 to 50.
In a preferred embodiment a ranges from 50 to 100.
In a preferred embodiment z is 18.
In a preferred embodiment z is 31.
In a preferred embodiment c ranges from 1 to 50.
In a preferred embodiment c ranges from 50 to 100.

EXAMPLES

Silicone Polymers

The silicone polymers useful as raw materials for the preparation of the compounds of the present invention are items of commerce and are commercially available from a variety of sources including Siltech LLC Dacula, Ga.

Group 1—Internal Silanic Hydrogen Compounds

The compounds of this group conform to the following structure:

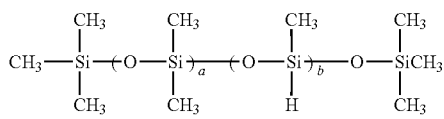

wherein:
a is an integer ranging from 0 to 2,000;
b is an integer ranging from 1 to 50.

Examples 1-7

| Example | a | b |
|---------|------|----|
| 1 | 0 | 1 |
| 2 | 10 | 10 |
| 3 | 20 | 5 |
| 4 | 50 | 10 |
| 5 | 100 | 20 |
| 6 | 1000 | 30 |
| 7 | 2000 | 50 |

Group 2—Terminal Silanic Hydrogen Compounds

The compounds of this group conform to the following structure:

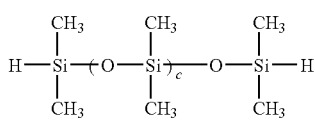

wherein:
c is an integer ranging from 0 to 2,000.

Examples 8-15

| Example | c |
|---|---|
| 8 | 0 |
| 9 | 2 |
| 10 | 5 |
| 11 | 20 |
| 12 | 50 |
| 13 | 100 |
| 14 | 1000 |
| 15 | 2000 |

Vinyl Ethers

Vinyl Ethers are items of commerce commercially available from BASF and ISP and conform to the following structure:

$CH_2=CH-O-(CH_2)_z-CH_3$;

wherein;
z is an integer ranging from 0 to 44;

Examples 16-20

| Example | z |
|---|---|
| 16 | 0 |
| 17 | 3 |
| 18 | 11 |
| 19 | 18 |
| 20 | 44 |

Hydrosilylation

Hydrosilylation is a process that reacts terminal vinyl compounds with silanic hydrogen to obtain a Si—C bond. References to this reaction, incorporated herein by reference, include:

U.S. Pat. Nos. 3,715,334 and 3,775,452 to Karstedt, shows the use of Pt(O) complex with vinylsilicon siloxane ligands as an active hydrosilylation catalyst.

Additional platinum complexes, such as complexes with platinum halides are shown by, U.S. Pat. No. 3,159,601 Ashby and, U.S. Pat. No. 3,220,972, to Lamoreaux.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

General Procedure

To a suitable flask equipped with heating, cooling and agitation is added the specified number of grams of the silanic hydrogen compound (Examples 1-15). The mass is mixed well. To that mixture is added the specified number of grams of the vinyl compound (Example 16-20). The reaction mass is mixed well until homogeneous. To that mixture is added 0.1% Karstedt catalyst, which is commercially available from Geleste. The agitation is stopped and the reaction begins. An exotherm is noted and the temperature is increased to 120° C. and held for 4 hours. Once the concentration of silanic hydrogen is below 0.5% is considered complete. The product is used without additional purification.

| | Silanic Hydrogen Compound | | Vinyl Ether | |
|---|---|---|---|---|
| Example | Example | Grams | Example | Grams |
| 22 | 1 | 224 | 16 | 70 |
| 23 | 2 | 150 | 17 | 120 |
| 24 | 3 | 389 | 18 | 256 |
| 25 | 4 | 446 | 19 | 372 |
| 26 | 5 | 7420 | 20 | 809 |
| 27 | 6 | 2532 | 20 | 809 |
| 28 | 7 | 214 | 19 | 372 |
| 29 | 8 | 68 | 18 | 256 |
| 30 | 9 | 142 | 17 | 120 |
| 31 | 10 | 253 | 16 | 70 |
| 32 | 11 | 808 | 16 | 75 |
| 33 | 12 | 1918 | 17 | 125 |
| 34 | 13 | 4727 | 18 | 268 |
| 35 | 14 | 37068 | 19 | 388 |
| 36 | 15 | 74081 | 20 | 815 |

Applications

The compounds of the resent invention have improved oil solubility and can be added to formulated products like lipsticks and pigmented products to minimize syneresis.

The compounds of the present invention can be added to oils to make serums. They enhance the spread and provide unique cosmetic aesthetic, since they are not as hard as the same material made with alkyl groups.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A process for conditioning hair and skin which comprises contacting the hair or skin with an effective conditioning concentration of an ether alkyl silicone conforming to the following structure;

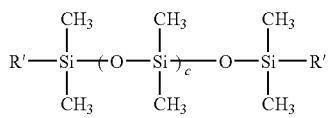

wherein:
R' is $-(CH_2)_2-O-(CH_2)_z-CH_3$;
z is an integer ranging from 0 to 44;
c is an integer ranging from 0 to 2,000;
said effective conditioning concentration ranging from 0.1 to 20% by weight.

2. A process of claim 1 wherein c ranges from 1 to 50.

3. A process of claim 1 wherein c ranges from 50 to 100.

4. A process of claim 1 wherein z is 18.

5. A process for conditioning hair and skin which comprises contacting the hair or skin with an effective conditioning concentration of to a ether alkyl silicone conforming to the following structure;

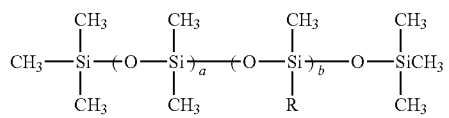

wherein:

R is —(CH$_2$)$_2$—O—(CH$_2$)$_z$—CH$_3$;

z is an integer ranging from 31 to 44;

a is an integer ranging from 0 to 2,000;

b is an integer ranging from 1 to 50;

said effective conditioning concentration ranging from 0.1 to 20% by weight.

6. An ether alkyl silicone of claim 5 wherein z is 31.

* * * * *